United States Patent [19]

Kerschner et al.

[11] Patent Number: 5,280,117

[45] Date of Patent: Jan. 18, 1994

[54] PROCESS FOR THE PREPARATION OF MANGANESE BLEACH CATALYST

[75] Inventors: Judith L. Kerschner, Ridgewood; Vikki Chin Quee-Smith, Teaneck, both of N.J.

[73] Assignee: Lever Brothers Company, a Division of Conopco, Inc., New York, N.Y.

[21] Appl. No.: 942,574

[22] Filed: Sep. 9, 1992

[51] Int. Cl.$^5$ ............... C07D 225/02; B01J 31/00
[52] U.S. Cl. ................... 540/465; 502/167; 540/486; 540/541; 544/181; 544/225; 556/45; 556/50
[58] Field of Search ............ 540/465, 486, 541; 544/181, 225; 546/2, 12; 548/102, 108, 402; 556/45, 50; 502/167

[56] References Cited

U.S. PATENT DOCUMENTS

| | | | |
|---|---|---|---|
| 4,626,373 | 12/1986 | Finch et al. | 252/96 |
| 4,728,455 | 3/1988 | Rerek | 252/99 |
| 5,153,161 | 10/1992 | Kerschner et al. | 502/167 |
| 5,194,416 | 3/1993 | Jureller et al. | 502/167 |

FOREIGN PATENT DOCUMENTS

| | | |
|---|---|---|
| 42939/89 | 5/1990 | Australia . |
| 0306089 | 3/1989 | European Pat. Off. . |
| 0458397 | 11/1991 | European Pat. Off. . |
| 0458398 | 11/1991 | European Pat. Off. . |
| 0369841 | 5/1990 | Japan . |

OTHER PUBLICATIONS

J. Am. Chem. Soc. (Weighardt et al) 1988, vol. 110, pp. 7398-7411.

J. Chem. Soc. Chem. Comm. (Weighardt et al) 1988, pp. 1145-1146.

Primary Examiner—Mukund J. Shah
Assistant Examiner—Y. N. Gupta
Attorney, Agent, or Firm—Milton L. Honig

[57] ABSTRACT

A process is described for the preparation of a manganese complex catalyst having the formula:

[LMn(OR)$_3$]Y, wherein Mn is manganese in the +4 oxidation state;
R is a $C_1$-$C_{20}$ radical selected from the group consisting of alkyl, cycloalkyl, aryl, benzyl and radical combinations thereof;
at least two R radicals may also be connected to one another so as to form a bridging unit between two oxygens that coordinate with the manganese;
L is a ligand selected from a $C_3$-$C_{60}$ radical having at least 3 nitrogen atoms coordinating with the manganese; and
Y is an oxidatively-stable counterion;
the process includes the steps of:
(i) reacting in an nonaqueous alcoholic medium a manganese (II) salt with the ligand L to form a manganese coordinated substance, a counterion salt $M_zY_q$ being present wherein M is selected from the group consisting of metallic, ammonium and alkanolammonium ions, z is an integer ranging from 1 to 4 and q is an integer from 1 to 4; and
(ii) oxidizing the manganese coordinated substance with an oxidizing agent while simultaneously basifying the medium to thereby form the manganese complex catalyst.

6 Claims, No Drawings

PROCESS FOR THE PREPARATION OF MANGANESE BLEACH CATALYST

BACKGROUND OF THE INVENTION

1. Field of the Invention

The invention concerns an improved synthesis of a manganese complex useful as a bleach catalyst.

2. The Related Art

Peroxide bleaching agents for use in laundering have been known for many years. Such agents are effective in removing stains, such as tea, fruit and wine stains, from clothing at or near boiling temperatures. The efficacy of peroxide bleaching agents diminishes sharply at temperatures below 60° C.

It is known that many transition metal ions catalyze the decomposition of $H_2O_2$ and $H_2O_2$-liberating percompounds, such as sodium perborate. It has also been suggested that transition metal salts together with a chelating agent be employed to activate peroxide compounds to render them usable for satisfactory bleaching at lower temperatures. Not all combinations of transition metals with chelating agents are suitable for improving the bleaching performance of peroxide compound bleaches. Many combinations indeed show no effect, or even a worsening effect, on the bleaching performance. A recent advance in this technology was described in copending U.S. Patent application No. 07/798,396, filed Nov. 26, 1991. Therein was reported a class of highly active bleaching catalysts in the form of a mononuclear manganese complex having the general formula:

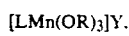

[LMn(OR)$_3$]Y.

especially the species:

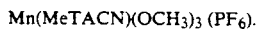

Mn(MeTACN)(OCH$_3$)$_3$ (PF$_6$).

Related dinuclear manganese complexes such as the species Mn(MeTACN)$_2$($\mu$-O)$_3$(PF$_6$)$_2$·H$_2$O, have been synthesized and described by K. Wieghardt in the "Journal of the American Chemical Society", 1988, Vol. 110, No. 22, page 7398, as well as in the "Journal of the Chemical Society—Chemical Communications", 1988, page 1145.

The synthesis route for dinuclear complexes as described in the above art involves the reaction in aqueous medium of a manganese (III)-compound, e.g. Mn (III)-triacetate, with a proper nitrogen-containing ligand, e.g. 1,4,7-trimethyl-1,4,7triazacyclononane, using an ethanol/water mixture as the solvent. A drawback of the aforementioned process is that only low yields of the dinuclear Mn (III)-complex can be achieved. Another problem associated with the process of the art is that, owing to the slow crystallization of the product, long reaction times are necessary. Still another problem is that besides crystallization of the desired product, decomposition also seems to occur, yielding manganese dioxide which contaminates the product. Therefore, a purification process is required when the product is to be converted into the dinuclear Mn (IV)-complex.

More recently there was reported in co-pending U.S. Patent application Ser. No. 07/798,477 filed Nov. 26, 1991, a process for the preparation of dinuclear manganese complex catalysts wherein a four-step procedure is outlined. Therein a manganese II salt and a ligand L are reacted to form a manganese coordinated substance. In a second and third step, the substance is oxidized and then basified to a pH of at least 10.5, respectively. The fourth step requires contacting the basified reaction mixture with a further oxidizing agent so as to form the final manganese complex catalyst. Yields in the 60% range are thereby achieved.

During investigation of synthesis routes to the dinuclear manganese complex, it was discovered that the use of dry methanol would produce the mononuclear complex whereas addition of water would result in formation of the dinuclear complex. Unfortunately, this route to the mononuclear complex provided yields below 30%, most often below 20%. Improvements in yield and reduction in processing costs would, therefore, be highly desirable.

Accordingly, it is an object of the present invention to provide an improved method for the preparation of manganese (IV) mononuclear complexes.

A more specific object of the present invention is to provide an improved method for preparing manganese complexes of high purity in high yields, which can be converted into the corresponding mononuclear manganese (IV)-complexes by oxidation.

These and other objects of the present invention will become more readily apparent from the detailed description and examples given hereafter.

SUMMARY OF THE INVENTION

A process is described for the preparation of a manganese complex catalyst having the formula:

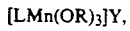

[LMn(OR)$_3$]Y, wherein Mn is manganese in the +4 oxidation state;

R is a $C_1$–$C_{20}$ radical selected from the group consisting of alkyl, cycloalkyl, aryl, benzyl and radical combinations thereof;

at least two R radicals may also be connected to one another so as to form a bridging unit between two oxygens that coordinate with the manganese;

L is a ligand selected from a $C_3$–$C_{60}$ radical having at least 3 nitrogen atoms coordinating with the manganese; and Y is an oxidatively-stable counterion;

the process comprising the steps of:
(i) reacting in an nonaqueous alcoholic medium a manganese (II) salt with the ligand L to form a manganese coordinated substance, a counterion salt $M_zY_q$ being present wherein M is selected from the group consisting of metallic, ammonium and alkanolammonium ions, z is an integer ranging from 1 to 4 and q is an integer from 1 to 4; and
(ii) oxidizing the manganese coordinated substance with an oxidizing agent while simultaneously basifying the medium to thereby form the manganese complex catalyst.

DETAILED DESCRIPTION

Now it has been found that high yields of mononuclear manganese complexes of relatively high purity can be obtained in much shorter reaction time and essentially, in a single pot reaction through use of simple manganese (II) inorganic salts.

Accordingly, in its broadest aspect, the invention provides a process for preparation of mononuclear manganese complexes of the formula:

[LMn(OR)₃]Y, wherein Mn is manganese in the +4 oxidation state;

R is a $C_1-C_{20}$ radical selected from the group consisting of alkyl, cycloalkyl, aryl, benzyl and radical combinations thereof;

at least two R radicals may also be connected to one another so as to form a bridging unit between two oxygens that coordinate with the manganese;

L is a ligand selected from a $C_3-C_{60}$ radical having at least 3 nitrogen atoms coordinating with the manganese; and Y is an oxidatively-stable counterion.

The counterion Y needed for charge neutrality of the complex is generally provided by carrying out the complexation reaction in the presence of a counterion-forming salt. Though the type of the counterion-forming salt, e.g. chlorides; sulphates; nitrates; methylsulphates; and surfactants such as alkyl sulphates, alkyl sulphonates, alkylbenzene sulphonates, tosylates, trifluoromethyl sulphonates, perchlorates, $NABH_4$ and $KPF_6$, is not critical for the conversion, some salts are more preferred than others in terms of product properties or safety. For example, small counterions will produce oily liquids and perchlorates are potentially explosive and could become a severe hazard upon large-scale preparation. Preferred counterions are the large molecules from surfactants, especially tosylate. Particularly preferred counterions are $PF_6^-$ and sulphate.

The R group is preferably a lower alkyl radical such as methyl and ethyl derivable from methyl and ethyl alcohol. Two R radicals may also be connected to one another so as to form a bridging unit. Illustrative is the ethylene unit derivable from ethylene glycol or propylene glycol.

Suitable and preferable ligands for use in the present invention are those which coordinate the three nitrogen atoms to one of the manganese centers, preferably being of a macrocyclic nature.

The nitrogen atoms can be part of tertiary, secondary or primary amine groups, but also part of aromatic ring systems, e.g. pyridines, pyrazoles, etc. or combinations thereof.

Examples of specific ligands most preferred are those having the structures:

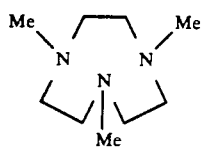
I

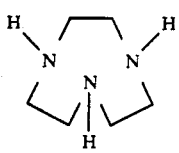
II

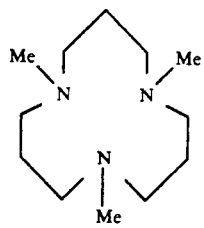
III

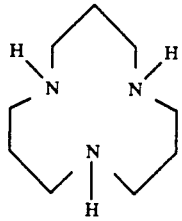
IV

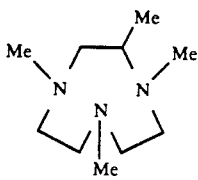
V

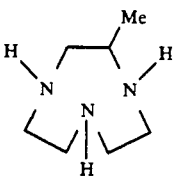
VI

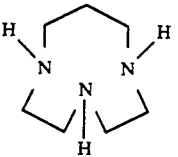
VII

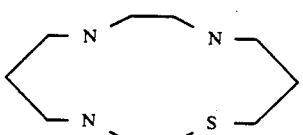
VIII

The most preferred ligands are I-V, with I being particularly preferred.

Ligand (I) is 1,4,7-trimethyl-1,4,7-triazacyclononane, coded as ME-TACN; ligand (II) is 1,4,7-triazacyclononane, coded as TACN; ligand (III) is 1,5,9-trimethyl-1,5,9-triazacyclododecane, coded as ME-TACD; ligand (V) is 2-methyl-1,4,7-trimethyl-1,4,7-triazacyclononane, coded as Me/Me-TACN; and ligand (VI) is 2-methyl-1,4,7-triazacyclononane, coded as ME-TACN.

Any of these complexes, either preformed or formed in situ during the washing process, are useful catalysts for the bleach activation of peroxy compounds over a wide class of stains at lower temperatures in a much more effective way than the Mn-based catalysts of the art hitherto known. Furthermore, these catalysts exhibit a high stability against hydrolysis and oxidation, even in the presence of oxidants such as hypochlorite.

Manganese complexes which are the object of the present synthesis and which are particularly preferred are those with the following structures:

$Mn(MeTACN)(OCH_3)_3(PF_6)$;
$[Mn(MeTACN)(OCH_3)_3]_2(SO_4)$; and
$Mn(MeTACN)(OCH_2CH_3)_3(PF_6)$.

An important advantage of the process according to the invention is that it can be performed in a single reactor without isolation of any intermediate products.

A first step of the process involves reacting a manganese (II) salt with a ligand L in the presence of a counterion salt $M_zY_q$. Suitable as manganese (II) salts are manganese chloride, manganese sulphate, manganese bromide and manganese nitrate, with the manganese chloride being preferred. The molar ratio of manganese (II) salt to ligand may range anywhere from 4:1 to 1:4, preferably from about 2:1 to about 1:1, optimally about 1.5:1 to 1:1. Relative molar ratios of the manganese (II) salt to the counterion salt will range from about 4:1 to 1:4, preferably from about 2:1 to about 1:2, optimally between about 1:1 and 1:2.

In a second and final step of the reaction, the manganese coordinated substance formed in the first step is oxidized. Oxidation can be performed with air, pure oxygen, hydrogen peroxide adducts such as urea peroxide, persalts such as sodium percarbonate and perborate, alkalimetal and alkaline earth metal peroxides, organic peracids and any combination thereof. Most preferred, however, as an oxidizing agent is solid sodium peroxide.

In the second step of the reaction, the reaction medium must be basified. Sodium hydroxide as generated from sodium peroxide is the preferred basifying agent. It is important that the reaction mixture of the second step simultaneously be provided with both the oxidizing and the basifying agents. The best procedure for this is to combine both within the same compound, i.e. sodium peroxide, only under such circumstances will high and reproducible yields be achieved.

Advantageously, upon reaction completion the resultant mixture is quenched with aqueous acid so as to lower pH to 9 or below, preferably between 7 and 9. Decomposition of the desired manganese complex catalyst is thereby avoided.

For purposes of this invention, there need be no isolation of any coordinated manganese intermediates. In fact, such isolation of a coordinated manganese intermediate is disadvantageous. Further, for purposes of this invention it is necessary to employ a nonaqueous (dry) alcoholic solvent system. Particularly useful is methanol. Choice of the solvent will determine the type of alkoxide substitution around the manganese. Ethanol is another preferred alcohol.

The following examples will more fully illustrate the embodiments of this invention. All concentrations presented are by weight unless otherwise indicated.

EXAMPLE 1

Preparation of $MnMeTACN(OCH_3)_3(PF_6)$

In a 250 ml round bottomed flask was added 0.74 g $NnCl_2$ dissolved in 80 ml methanol. Then 1.0 g METACN ligand, dissolved in 20 ml methanol, was added to the above solution and allowed to stir for 5–15 minutes. The mixture was then placed in an icebath at $-50°$ C. Thereafter 0.46 g sodium peroxide was slowly added to the mixture. After one hour of stirring the icebath was removed and the reaction was allowed to warm up to room temperature for another 1–2 hours. Finally, 1.0 g $NAPF_6$ was added to the mixture and the reaction was stirred until the salt dissolved (about ½ hour). The mixture was filtered and the filtrate was neutralized with dilute sulfuric acid. Then 50 ml milli-Q water was added to the neutralized filtrate and stirred for 10–15 minutes. Another filtration was performed on the mixture. Solvent was reduced through roto-evaporation to ⅓ of the mixturers former volume. Product crystals were obtained by filtration; they were characterized by uv-Vis spectrophotometry as $MnMeTACN(OCH_3)_3(PF_6)$.

EXAMPLE 2

Preparation of $MnMeTACN(OCH_2CH_3)_3PF_6$

In a 250 ml round bottomed flask was added 1.0 g METACN dissolved in 20 ml dry 200 proof ethanol. The solution was deoxygenated and stirred under $N_2$. Then 0.74 g $MnCl_2$ in 20 ml ethanol was added to the solution, and the mixture was placed in an icebath at around $-10°$ C. To the stirring, chilled mixture was added 0.44 g sodium peroxide and another 20 ml ethanol. After 2 hours the icebath was removed and the reaction was allowed to warm to room temperature for about 2 hours. Finally, 1.0 g $NAPF_6$ salt, predissolved in 40 ml ethanol, was added to the mixture. The resultant solution mixture was allowed to stir for an additional 30 minutes. Thereafter, the mixture was filtered and placed in a freezer to promote crystallization. A brown crystalline material was isolated which, upon analysis by UV-Vis spectrophotometry, was characterized as $MnMeTACN(OCH_2CH_3)_3(PF_6)$.

EXAMPLE 3

Comparison of % Yields of Different Methods to Obtain $MnMeTACN(OCH_3)_3(PF_6)$

There are several preparations for synthesizing $Mn(MeTACN)(OCH_3)_3$ $(PF_6)$ and the different oxidizing agents are listed below with the various isolated yields as a comparison.

| Method | % Yield |
| --- | --- |
| NaOMe | 16–27 |
| NaOH in air | 17–22 |
| $Na_2O_2$ (not neutralized) | 23–38 |
| $Na_2O_2$ (neutralized) | 45–50 |

The last entry of the Table reflects a reaction wherein subsequent to completion, the resultant mixture was quenched by lowering pH to below 9 by addition of aqueous acid. Decomposition of the desired manganese complex catalyst was thereby avoided. Yields improved from the 23%–38% range for nonquenched reactions to the much higher 45%–50% range.

The foregoing description and examples illustrate selected embodiments of the present invention. In light thereof, various modifications will be suggested to one skilled in the art, all of which are within the spirit and purview of this invention.

What is claimed is:

1. A process for the preparation of a manganese complex catalyst having the formula:

$[LMn(OR)_3]Y$, wherein Mn is manganese in the +4 oxidation state;

is a $C_1$-$C_{20}$ radical selected from the group consisting of alkyl, cycloalkyl, aryl, benzyl and radical combinations thereof;

at least two R radicals may also be connected to one another so as to form a bridging unit between two oxygens that coordinate with the manganese;

L is a ligand having at least 3 nitrogen atoms that are part of a 9 to 14 member ring system and coordinating with the manganese; and Y is an oxidatively-stable counterion;

the process comprising the steps of:

(i) reacting in an nonaqueous alcoholic medium a manganese (II) salt with the ligand L to form a manganese coordinated substance, a counterion salt $M_zY_q$ being present wherein M is selected from the group consisting of metallic, ammonium and alkanolammonium ions, z is an integer ranging from 1 to 4 and q is an integer from 1 to 4; and (ii) oxidizing the manganese coordinated substance with an oxidizing agent while simultaneously basifying the medium to thereby form the manganese complex catalyst.

2. A method according to claim 1 wherein the oxidizing agent is sodium peroxide.

3. A method according to claim 1 wherein basification is achieved with sodium hydroxide derived from sodium peroxide.

4. A method according to claim 1 wherein the manganese complex has the formula $Mn(MeTACN)(OCH_3)_3Y$.

5. A method according to claim 1 wherein the manganese complex has the formula $Mn(MeTACN)(OCH_2CH_3)_3Y$.

6. A method according to claim 1 wherein subsequent to step (ii) and formation of the manganese complex catalyst, the pH of the medium is quenched with aqueous acid to a level no higher than pH 9 and thereafter the catalyst is separated as a solid from the medium.

* * * * *